United States Patent [19]

Hommes

[11] Plant 4,279

[45] Jul. 11, 1978

[54] DUTCH IRIS PLANT NAMED APOLLO

[75] Inventor: Gerard Dirk Hommes, Heiloo (N.H.), Netherlands

[73] Assignee: Marlboro Bulb Farms, Wilmington, N.C.

[21] Appl. No.: 836,236

[22] Filed: Sep. 23, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Rummler & Snow

[57] ABSTRACT

A new variety of Dutch iris plant suitable for greenhouse culture or outdoors when the temperature and light conditions are suitable and proper for the commercial production of cut flowers, particularly distinguished by its very large blossom, unusual orange-yellow center blotch of its falls and terminating in a light yellow blotch, and its white standards. This plant is also characterized by its extremely large and robust stalk which carries its flower much better than normal varieties, the flower lasting longer than normal varieties, blooms earlier, and the buds are very tight whereby this variety may be shipped successfully over longer distances.

1 Drawing Figure

BACKGROUND OF THE NEW PLANT

My new variety of Dutch iris plant was discovered by me on June 10, 1954, in Heiloo, Holland, on the nursery of Hommes Bulb Co. B.V. as the result of breeding efforts carried on to produce a variety with the same early blooming time as the parent Wedgwood (unpatented) but with a different color, and using the pollen parent Angels Wings (not patented). Because of the distinctive and attractive color, it was taken by me for propagation and successive generations of the resulting plant propagated by root division and grown in the fields and greenhouse at Heiloo, Holland, have demonstrated that its novel color characteristics are firmly fixed and hold true.

DESCRIPTION OF THE DRAWING

My new variety of Dutch iris plant is illustrated by the accompanying photographic drawing which shows, in full color, the form of the fully opened flower, and bud, the colors being as nearly true as it has been possible to obtain by conventional photographic procedures.

DESCRIPTION OF THE PLANT

The following description of my new Dutch iris plant sets out its characteristics in detail and comprises data from observations of greenhouse plants and open field plants grown in Heiloo, Holland, from 1954 to date, the color designations being according to the Royal Horticultural Colour Chart produced by The Royal Horticultural Society at London, England, except where general color terms of ordinary dictionary significance are obvious.

THE PLANT

Origin: Seedling.

Parentage:

*Seed parent.*—Wedgwood (tetraploid) (not patented).

*Pollen parent.*—Angels Wings (not patented).

Classification:

*Botanic.*—Dutch Iris (*Iris hollandica*).

*Commercial.*—Wedgwood Hybrid.

Form: Single stem.

Habit: Upright.

Growth: Rapid.

Height: 2 feet, 7 inches average.

Stem: Quite large, straight upwards, long.

*Strength.*—Sturdy and strong.

Foliage: Quantity — normal.

*Shape.*—Slender.

*Size of leaf.*—8 to 10 inches long.

*Texture.*—Smooth.

*Upper color.*—Green.

*Under color.*—Grayish green.

Bulbs:

*Color.*—White with brown skin.

*Size.*—From ½ inch to 1½ inches.

THE BUD

Size:

*Length.*—4 inches.

*Diameter.*—¾ inches to 1 inch.

Form: Elongated oval shape and pointed.

Rate of opening: Normal.

Color: In tight bud stage, buttercup yellow. At the beginning of opening, yellow and white.

Peduncle:

*Hairy.*—No.

*Strength.*—Erect.

*Color.*—Light green.

THE FLOWER

Blooming habit: Once each year with normal storing and planting in spring. May bloom the year around when bulbs are prepared to bloom at a specific time in controlled environment.

Size: Very large, having a diameter and depth of up to 6 inches.

Borne: Singly.

Shape: When blooms first open, the standards are upwards and the falls are rounded and point downwardly. Bridge extended horizontally outwards. At maturity, falls point downwards. Bridge extended horizontally outwards.

Petalage:

*Number.*—3 falls and 3 standards.

*Arrangement.*—Falls at 120° position from each other. Standards intermittent at 120° position.

*Color.*—Falls-Body: Yellow (5C). Center blotch: Orange yellow (17A).

*Standards.*—Body: White (155C). Base: White with bluish cast (100D).

*Reverse side.*—Falls: Light yellow. Standards: White (155C).

*Bridge.*—Creamy yellow (10D).

Texture: Soft, i.e., falls and standards.

Appearance: Satiny.

Number of falls: Three, each somewhat concave oblong in shape.

*Size.*—Average; $1\frac{3}{4} \times 2\frac{1}{4}$ inches.

*Color.*—Yellow (5C). Medium stripe on inside of outer petal, yellow (9A); on outside of outer petal, greenish yellow (151D). To both sides of the stripe is a distinctive nerve pattern which merges into the white color (155C) of the outer petal. Along the outer edges of the petal, the color turns to light yellow (5C).

Standards: Three.

*Size.*—$3\frac{1}{4}$ inches long; $\frac{3}{4}$ inch wide.

*Color.*—Same as under Petalage.

REPRODUCTIVE ORGANS

Stamens: Epigynous of 1 inch length and three in number.

Filaments: One inch in length.

*Color.*—White (155A) with yellow (7A) base.

Pollen: Abundant.

*Color.*—Yellow.

Pistils: Three in number, curved, convex, oblong.

*Length.*—$3\frac{1}{2}$ inches.

Stigmas: Three in number per flower.

*Color.*—Ivory white (155A).

Comb: Fine ruffled, light yellow color (2D).

Characteristics of ovaries: One ovary per flower consisting of three equal sections located 120° from each other, each section ending at top where pistils begin.

FRUIT

Fertile: No, due to variety being a triploid genetically.

Shape: Rather elongated oblong.

Color at maturity: Green.

This new variety of Dutch iris generally resembles Angels Wings (not patented). This new variety is a triploid and its cells contain $1\frac{1}{2}$ times the number of chromosomes than is normal to other varieties of the species. The bulbs are medium size for producing flowers the next year and are only 8 centimeters in circumference. Normal bulbs of the species are generally much larger for other varieties of the species. The flower stalk is extremely large and robust and carries a flower which is much larger than the average for other varieties of the species. The blooming time in the field under normal growing conditions is much earlier than other varieties within the species. The flower buds open extremely well, even when the buds are very tight at the time of harvesting the flower crop. Therefore this variety can be shipped over long distances with great success.

I claim:

1. A new and distinctive variety of iris plant substantially as herein shown and described, characterized by the distinctive colored falls having an orange-yellow blotch and light yellow body and by its white standards, by its very large flower, by its tight buds allowing for long distance shipping before the bud opens, by its fast early growing habit, its strong large upright stems, with little or no crinkling of the falls and upright standards, and by its minimum size bulbs and its capability of blooming at any specific time in controlled environment.

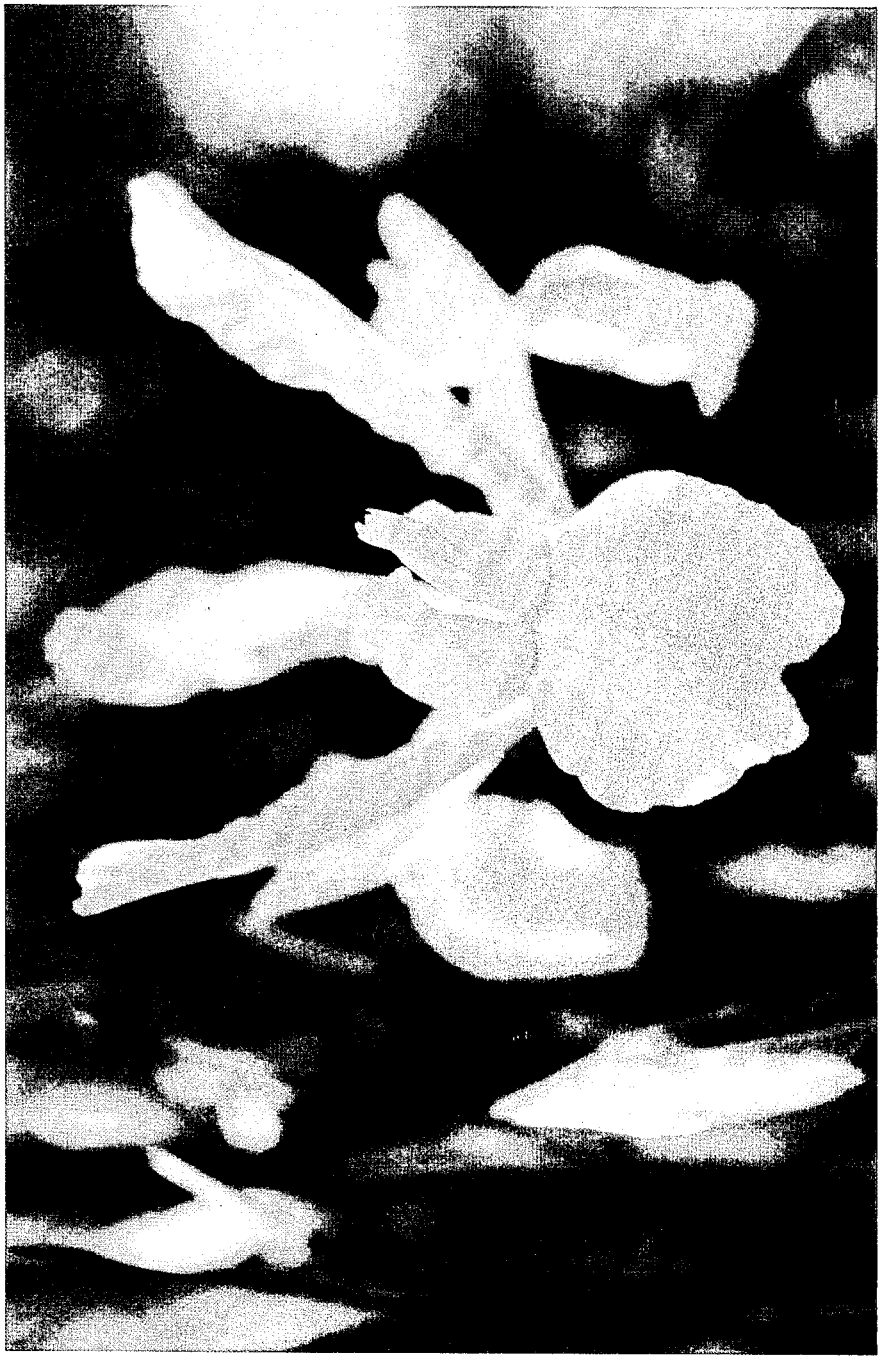

* * * * *